US008670813B2

(12) United States Patent
Tang

(10) Patent No.: US 8,670,813 B2
(45) Date of Patent: *Mar. 11, 2014

(54) SYSTEMS AND METHODS FOR ANALYSIS AND TREATMENT OF AN OCCLUDED BODY LUMEN

(75) Inventor: Jing Tang, Arlington, MA (US)

(73) Assignee: Angiolight, Inc., Medford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/600,718

(22) Filed: Aug. 31, 2012

(65) Prior Publication Data

US 2012/0330166 A1  Dec. 27, 2012

Related U.S. Application Data

(63) Continuation of application No. 12/579,751, filed on Oct. 15, 2009, now Pat. No. 8,260,390.

(60) Provisional application No. 61/105,585, filed on Oct. 15, 2008, provisional application No. 61/109,704, filed on Oct. 30, 2008, provisional application No. 61/180,068, filed on May 20, 2009.

(51) Int. Cl.
*A61B 5/00* (2006.01)
*A61B 6/00* (2006.01)

(52) U.S. Cl.
USPC ............................ 600/341; 600/478

(58) Field of Classification Search
USPC ..................... 600/341, 473, 478
See application file for complete search history.

(56) References Cited

U.S. PATENT DOCUMENTS

| 5,647,359 A * | 7/1997 | Kohno et al. ............... 600/341 |
| 6,842,639 B1 * | 1/2005 | Winston et al. ............ 600/478 |
| 8,260,390 B2 * | 9/2012 | Tang ........................... 600/341 |
| 2002/0156380 A1 * | 10/2002 | Feld et al. .................. 600/473 |
| 2008/0139930 A1 * | 6/2008 | Weese et al. ............... 600/424 |
| 2010/0069760 A1 * | 3/2010 | Tang ........................... 600/478 |
| 2010/0094109 A1 * | 4/2010 | Tang ........................... 600/341 |

* cited by examiner

Primary Examiner — William B Perkey
(74) Attorney, Agent, or Firm — Onello & Mello LLP

(57) ABSTRACT

Systems and methods are provided for probing an occluded body lumen, including a flexible conduit insertable into the body lumen, at least one delivery waveguide and at least one collection waveguide integrated with the flexible conduit and arranged to deliver and collect radiation about a distal end of said flexible conduit, at least one radiation source connected to a transmission input of the at least one delivery waveguide, at least one optical detector connected to a transmission output of at least one collection waveguide, a spectrometer connected with the at least one optical detector, and constructed and arranged to scan radiation and perform spectroscopy, and a controller programmed to process data from said spectrometer and provide information for directing said flexible conduit through obstacles within the occluded body lumen.

30 Claims, 9 Drawing Sheets

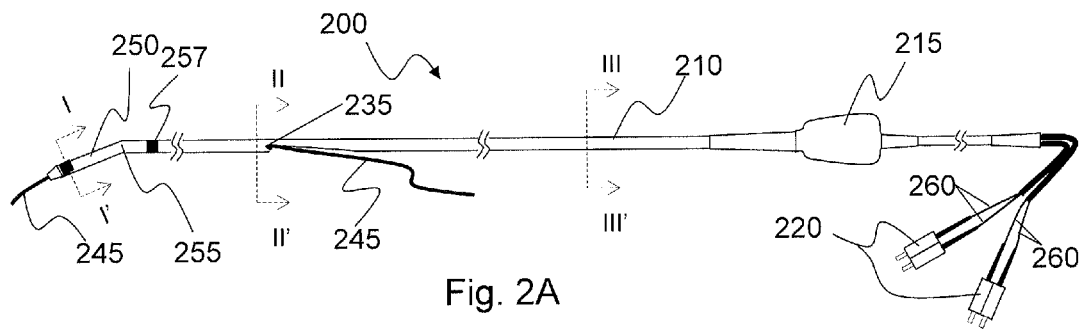
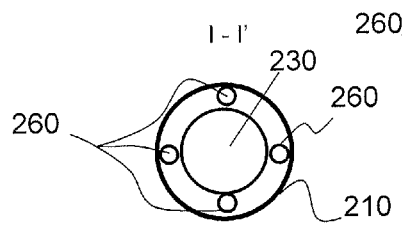
Fig. 2B
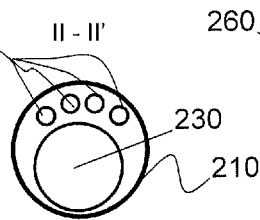
Fig. 2C
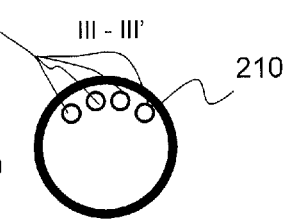
Fig. 2D
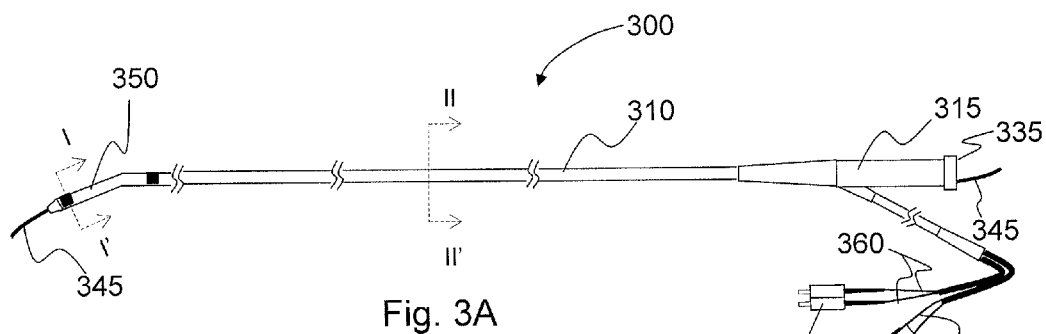
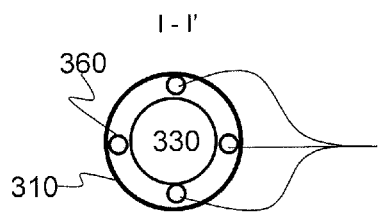
Fig. 3B
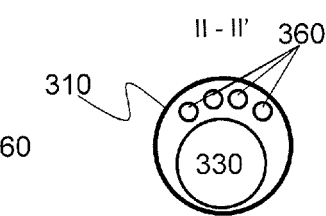
Fig. 3C

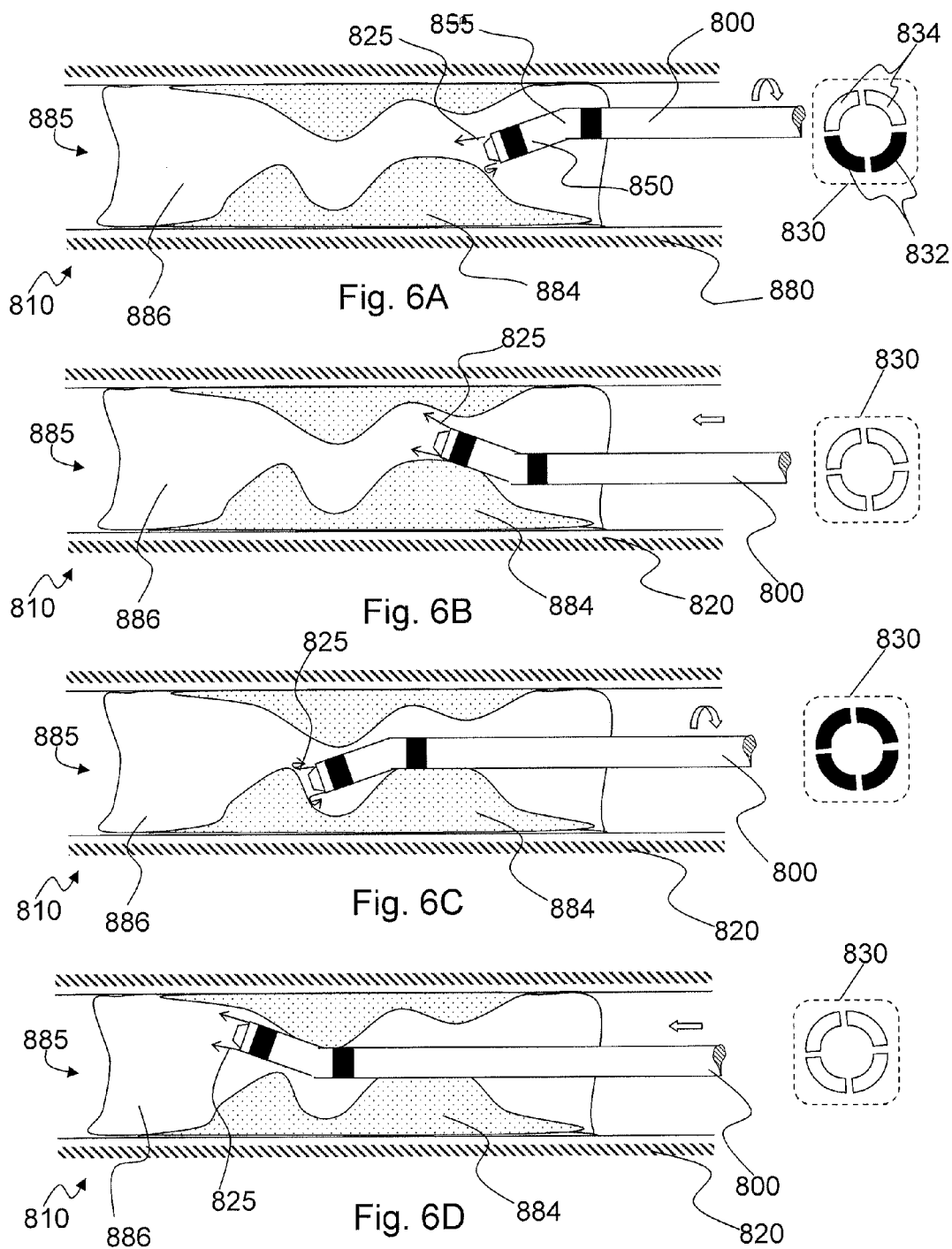

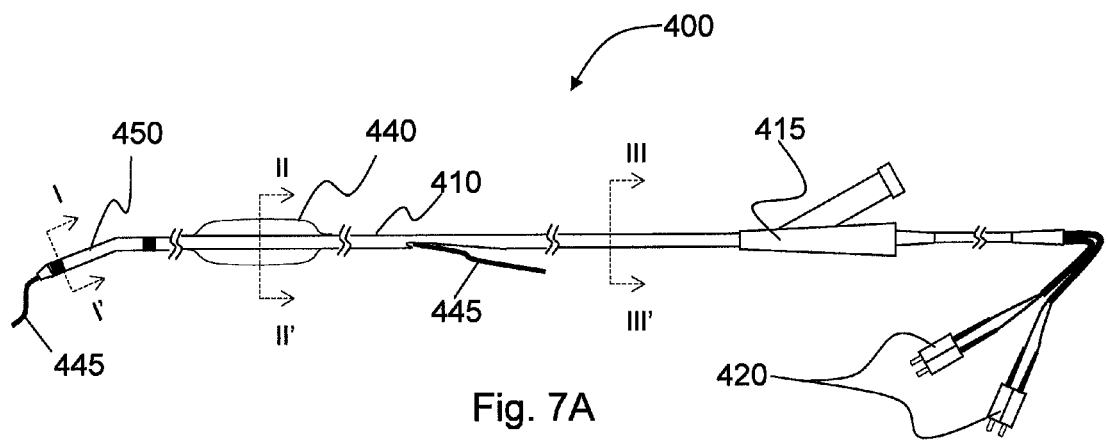
Fig. 7A
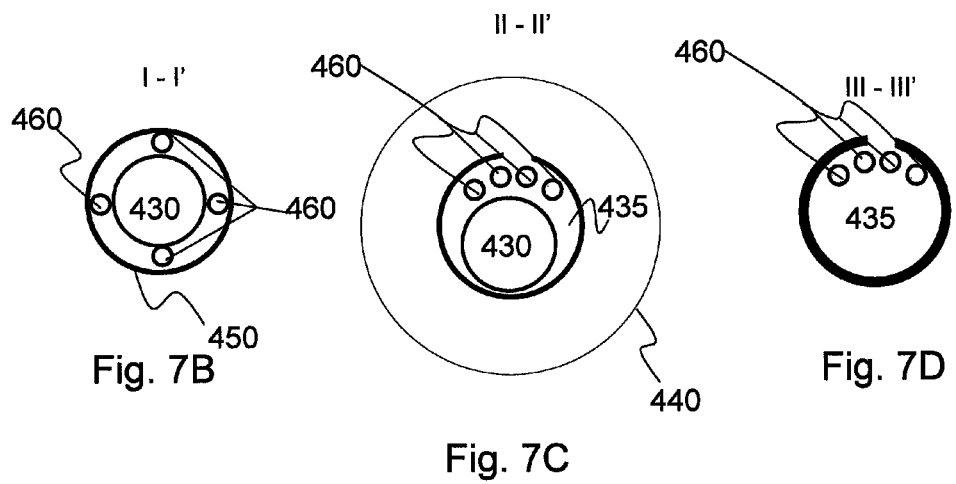
Fig. 7B
Fig. 7C
Fig. 7D

SYSTEMS AND METHODS FOR ANALYSIS AND TREATMENT OF AN OCCLUDED BODY LUMEN

RELATED APPLICATIONS

This application is a continuation application of U.S. Ser. No. 12/579,751 which claims the benefit of U.S. Provisional Patent Application No. 61/105,585, filed Oct. 15, 2008, U.S. Provisional Patent Application No. 61/109,704, filed Oct. 30, 2008, and U.S. Provisional Patent Application No. 61/180,068, filed May 20, 2009, the contents of each of which are herein incorporated by reference. This application is related to U.S. patent application Ser. No. 11/537,258, filed on Sep. 29, 2006, published as Patent Application Publication No. 2007/0078500, U.S. patent application Ser. No. 11/834,096, filed on Aug. 6, 2007, published as Patent Application Publication No. 2007/0270717, U.S. Patent Application No. 61/019,626, filed Jan. 8, 2008, U.S. Patent Application No. 61/025,514, filed Feb. 1, 2008, and U.S. Patent Application No. 61/082,721, filed Jul. 22, 2008, the entire contents of each of which are herein incorporated by reference.

BACKGROUND OF THE INVENTION

1. Field of the Invention

Embodiments of the present invention are directed to systems and methods for the analysis and treatment of a lumen. More particularly, the present invention relates to a catheter system that is used to perform methods for the analysis and/or treatment of an occluded lumen.

2. Description of the Related Art

With the continual expansion of minimally-invasive procedures in medicine, one procedure that has been highlighted in recent years has been percutaneous transluminal angioplasty, or "PTA," which can be used for treating diseased and partially blocked vessels such as those associated with atherosclerosis. The most prevalent use of this procedure is in the coronary arteries, the procedure more specifically called a percutaneous coronary transluminal angioplasty, or "PTCA". These procedures utilize a flexible catheter with an inflation lumen to expand, under relatively high pressure, a balloon at the distal end of the catheter to expand a stenotic lesion.

The PTA and PTCA procedures are now commonly used in conjunction with expandable tubular structures known as stents and an angioplasty balloon is often used to expand and permanently place the stent within the lumen. An angioplasty balloon utilized with a stent is referred to as a stent delivery system. An angioplasty balloon catheter is routed into place in a target vessel through a series of interconnected vessels, generally with the aid of a guidewire and fluoroscope.

In some instances, a vessel is sufficiently blocked, e.g., with a chronic total occlusion (CTO), so that a PTA procedure is considered unsuitable because of potential complications such as a rupture of the vessel when guiding the catheter into place. Up to about 30% of coronary artery disease patients in need of treatment have CTOs. The unavailability of precise information about the complex shapes and content of CTO vessels and their lesions can make navigating a guidewire through them extremely difficult, slow, and/or risky. Other potentially less effective or more complex and costly treatments, e.g., bypass surgery, may be selected instead.

Other technologies used for traversing occluded vessels include optics-based guidance systems such as visual imaging, Optical Coherence Reflectometry (OCR), and Coherence Tomography (OCT). Since these systems typically collect coherent reflected light from the target vessel area, they can require complex, expensive optics and signal processing systems including image sensors, rotating optics, bundled optical arrays, and/or interferometers. These systems also generally do not provide much information beyond the immediate target surface. Obtaining information that goes deeper than the immediate vicinity of a catheter tip could provide useful information for navigating through blocked or partially blocked regions and reduce the risk of ruptures. Ultrasonic sensors, e.g., the IVUS device marketed by Volcano Corporation of San Diego, Calif., have also been used but will generally provide even less information than an optical system can and are generally very expensive, require a separate invasive procedure, and usually include catheter tip sizes that make them inoperable in some small coronary vessels.

SUMMARY OF THE INVENTION

The systems and methods described in the present specification provide physicians performing an occluded-lumen traversal procedure with very useful information about the blocked region of the vessel with minimal additional procedure time and cost and reduced risk of perforation or rupture. Included are a number of embodiments of a distal fiber-optic configuration to optimally facilitate illumination of the lumen wall and collection of resultant optical signal with the use of diffuse reflectance spectroscopy. These implementations also provide manufacturability and relatively low-cost production required for a disposable medical device.

In an aspect of the invention, a system that probes and treats an occluded body lumen is provided that includes a flexible conduit that is suitable for insertion into a body lumen, the conduit elongated along a longitudinal axis and having a proximal end and a distal end. The system includes at least one delivery waveguide and at least one collection waveguide integrated with the flexible conduit and arranged to deliver and collect radiation about the distal end of said flexible conduit. The system includes at least one radiation source connected to a transmission input of the at least one delivery waveguide, the radiation source constructed and arranged to provide radiation at a wavelength in a range of about 250 to 2500 nanometers. The system includes at least one optical detector connected to a transmission output of the at least one collection waveguide. The system includes a spectrometer connected to the at least one optical detector, the spectrometer constructed and arranged to scan radiation and perform spectroscopy at the wavelength of the radiation provided by the radiation source. The spectrometer is configured to perform spectroscopy of at least one of the methods comprising fluorescence, light scatter, speckle correlometry, Raman, and diffuse reflectance spectroscopy. The system includes a controller programmed to process data from said spectrometer and provide information for directing said flexible conduit through obstacles within the occluded lumen.

In an embodiment, the spectrometer is configured to perform spectroscopy selected from the group of methods consisting of fluorescence and diffuse reflectance spectroscopy.

In an embodiment, the at least one delivery waveguide and at least one collection waveguide are configured to scan and collect radiation beyond the distal end of said flexible conduit.

In an embodiment, the spectrometer and controller are configured for measuring the presence of blood components beyond the distal end of said flexible conduit. In an embodiment, the blood components include hemoglobin. In an embodiment, the radiation source is configured to supply radiation including a wavelength of 450 nanometers and the spectrometer is configured and arranged to detect a fluorescence radiation including a wavelength of 520 nanometers.

In an embodiment, the spectrometer and controller are configured to perform diffuse reflectance spectroscopy scanning of one or more discrete wavelengths including one of about 532 nanometers.

In an embodiment, the spectrometer is configured to perform diffuse reflectance spectroscopy scanning one or more discrete wavelengths including scanning one or more discrete wavelengths including one of about 532 nanometers. In an embodiment, the wavelengths consists of one of about 532 nanometers, 407 nanometers, and at least one between about 800 and 1000 nanometers. In an embodiment, the one or more wavelengths consists of two wavelengths including at least one of about 532 nanometers.

In an embodiment, the system is programmed to calculate a ratio of absorbance data from the collection of said one or more wavelengths and compare the ratio with predetermined data including relationships between pre-calculated ratios of corresponding absorbance data to the presence of blood components within a lumen.

In an embodiment, the system includes a display connected to the controller, the controller and display are adapted to identify in real-time the areas of the occluded lumen that are traversable.

In an embodiment, the controller and display are adapted to demark identified areas of the occluded lumen represented by forward-positioned segments about the circumference of the conduit.

In an embodiment, the system includes a catheter of which the flexible conduit is a part.

In an embodiment, the catheter includes an angioplasty balloon. In an embodiment, a transmission output of the at least one delivery waveguide and a transmission input of the at least one collection waveguide is located within said angioplasty balloon.

In an embodiment, the flexible conduit has a maximum outer diameter of between about 0.5 and 0.67 millimeters.

In an embodiment, the flexible conduit includes has a maximum outer diameter of less than about 0.5 millimeters.

In an embodiment, the flexible conduit has a maximum outer diameter of about 1.35 millimeters or less.

In an embodiment, the flexible conduit is a guidewire. In an embodiment, the flexible conduit includes one or more fiber connectors detachable from the proximate end of the flexible conduit so as to allow said guidewire to completely pass through a catheter.

In an embodiment, the flexible conduit has a maximum outer diameter of about 0.4 millimeters or less.

In an embodiment, the flexible conduit has a maximum outer diameter of about 0.3 millimeters or less.

In an embodiment, the flexible conduit includes a distal end with a portion pre-bent at an angle so as to allow increased maneuverability through an occluded lumen.

In an embodiment, the portion pre-bent at an angle is bent at an angle between 15 and 45 degrees. In an embodiment, the angle is selected from 15, 30, and 45 degrees.

In an embodiment, the at least one delivery waveguide and at least one collection waveguide include fiber optic tips manufactured to emit or collect radiation circumferentially around approximately 90 degrees or more of the end of the fiber optic tips.

In an embodiment, a transmission output of at least one delivery waveguide is longitudinally separated from a transmission input of at least one collection waveguide.

In an embodiment, the at least one delivery waveguide and at least one collection waveguide consist of a single waveguide.

In another aspect of the invention, a method for directing a flexible conduit through obstacles within an occluded body lumen is provided, the method including providing a flexible conduit that is suitable for insertion into a body lumen, the flexible conduit integrated with at least one delivery waveguide arranged to deliver radiation about the distal end of said conduit and at least one collection waveguide arranged to collect radiation about the distal end of said conduit. The method further includes the step of maneuvering the conduit in proximity to an occluded region of the body lumen and executing spectroscopic analysis of the occluded region using radiation at a wavelength in a range of about 250 to 2500 nanometers. The spectroscopic analysis includes radiating areas of the occluded region with the radiation that is supplied at the transmission output of the at least one delivery waveguide, the supplied radiation distributed about the distal end of said flexible conduit and in which radiation is returned to the transmission input of the at least one collection waveguide. The spectroscopic analysis includes at least one of fluorescence, light scatter, speckle correlometry, Raman, and diffuse reflectance spectroscopy. The method further includes the step of processing data from said spectroscopic analysis in order to locate tissue and fluids ahead of said flexible conduit that is traversable and maneuvering the flexible conduit through traversable tissue and fluids.

In an embodiment, the spectroscopic analysis and processing data from spectroscopic analysis includes determining areas of blood components that allow relatively less impeded traversal of the flexible conduit. In an embodiment, determining areas of blood components that allow relatively less impeded traversal of the flexible conduit includes determining areas of relatively greater hemoglobin content. In an embodiment, the spectroscopic analysis includes delivering a wavelength of 450 nanometers and detecting a fluorescence radiation including a wavelength of 520 nanometers.

In an embodiment, the spectroscopic analysis includes scanning discrete wavelengths of about 532 nanometers, 407 nanometers, and between 800 and 1000 nanometers. In an embodiment, the spectroscopic analysis includes scanning two or less wavelengths including at least one of about 532 nanometers.

In an embodiment, the spectroscopic analysis includes calculating a ratio of absorbance data from the collection of said one or more wavelengths with predetermined data including relationships between pre-calculated ratios of corresponding absorbance data to the presence of blood components within a lumen.

In an embodiment, a display is provided that identifies in real-time the areas of the occluded lumen that are traversable.

In an embodiment, the areas of the occluded lumen are demarked by forward-positioned segments about the circumference of said conduit.

In an embodiment, flexible conduit includes a distal end with a portion pre-bent at an angle so as to allow increased maneuverability through the occluded lumen. In an embodiment, the portion with a pre-bent angle has an angle between 15 and 45 degrees. In an embodiment, the angle is selected from the group consisting of 15, 30, and 45 degrees.

In an embodiment, the step of maneuvering the flexible conduit through traversable tissue and fluids includes rotating said pre-bent portion toward an area identified as traversable.

In an embodiment, the flexible conduit includes an angioplasty balloon and the method further includes the step of inflating the angioplasty balloon after maneuvering the flexible conduit through the traversable tissue and fluids.

In an embodiment, the flexible conduit is a guidewire having a proximate end with detachable optical connectors in which the proximate end with detachable optical connectors is detached following the step of maneuvering the flexible conduit through the traversable tissue and fluids.

BRIEF DESCRIPTION OF THE DRAWINGS

The foregoing and other objects, features, and advantages of the invention will be apparent from the more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 2A is an illustrative view of a catheter instrument according to an embodiment of the present invention.

FIG. 2B is a cross-sectional view of the catheter instrument of FIG. 2A, taken along section lines I-I' of FIG. 2A.

FIG. 2C is a cross-sectional view of the catheter instrument of FIG. 2A, taken along section lines II-II' of FIG. 2A.

FIG. 2D is a cross-sectional view of the catheter instrument of FIG. 2A, taken along section lines of III-III' FIG. 2A.

FIG. 3A is an illustrative view of a catheter instrument according to an embodiment of the present invention.

FIG. 3B is a cross-sectional view of the catheter instrument of FIG. 3A, taken along section lines I-I' of FIG. 3A.

FIG. 3C is a cross-sectional view of the catheter instrument of FIG. 3A, taken along section lines II-II' of FIG. 3A.

FIGS. 6A-6D are illustrative views of the distal end of an instrument being positioned within a lumen according to an embodiment of the invention.

FIG. 7A is an illustrative view of an angioplasty balloon catheter instrument according to an embodiment of the present invention.

FIG. 7B is a cross-sectional view of the catheter instrument of FIG. 7A, taken along section lines I-I' of FIG. 7A.

FIG. 7C is a cross-sectional view of the catheter instrument of FIG. 7A, taken along section lines II-II' of FIG. 7A.

FIG. 7D is a cross-sectional view of the catheter instrument of FIG. 7A, taken along section lines III-III' of FIG. 4A.

DETAILED DESCRIPTION OF EMBODIMENTS OF THE INVENTION

Figure 1:
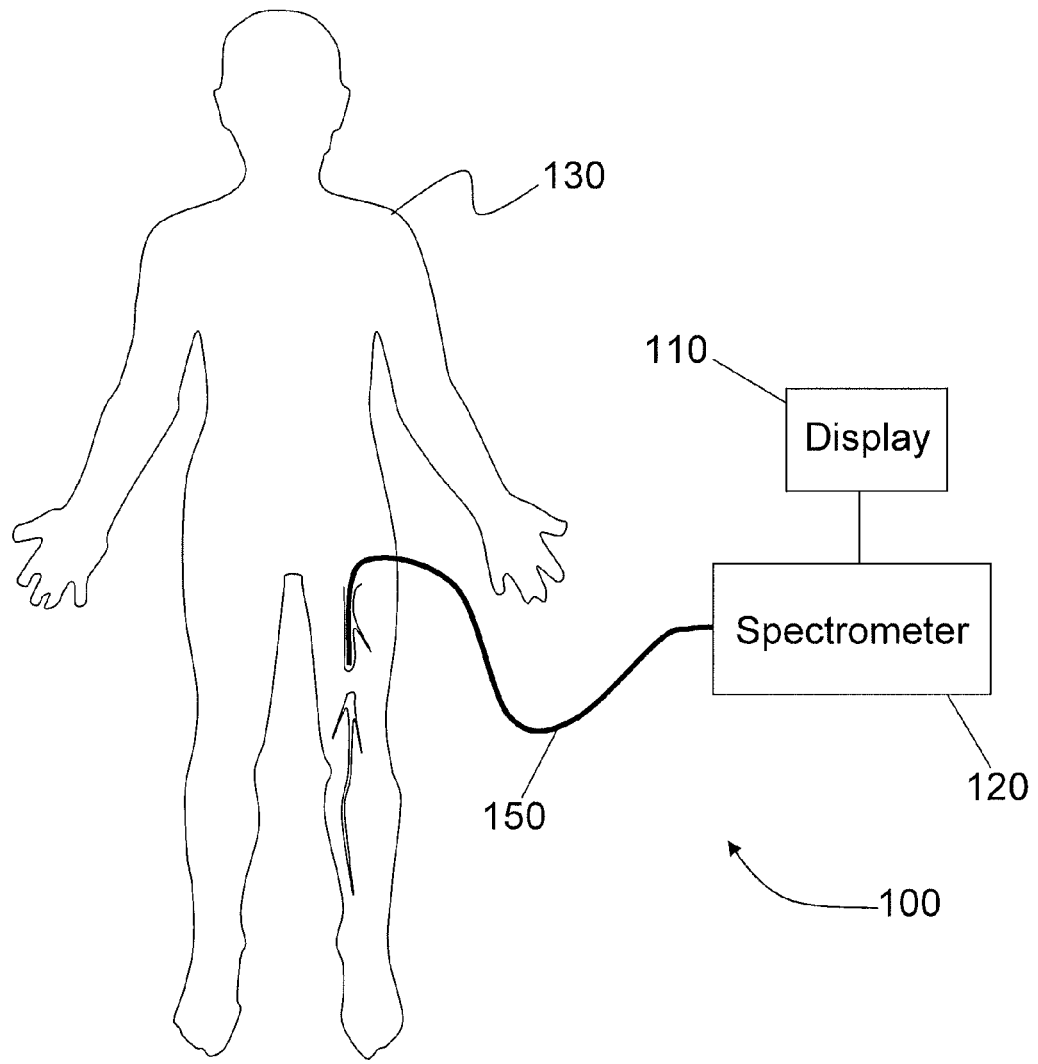
FIG. 1 is a schematic block diagram illustrating a system for analyzing and medically treating a lumen, according to an embodiment of the present invention.

The accompanying drawings are described below, in which example embodiments in accordance with the present invention are shown. Specific structural and functional details disclosed herein are merely representative. This invention may be embodied in many alternate forms and should not be construed as limited to example embodiments set forth herein.

Accordingly, specific embodiments are shown by way of example in the drawings. It should be understood, however, that there is no intent to limit the invention to the particular forms disclosed, but on the contrary, the invention is to cover all modifications, equivalents, and alternatives falling within the spirit and scope of the claims. Like numbers refer to like elements throughout the description of the figures.

It will be understood that, although the terms first, second, etc. may be used herein to describe various elements, these elements should not be limited by these terms. These terms are used to distinguish one element from another. For example, a first element could be termed a second element, and, similarly, a second element could be termed a first element, without departing from the scope of the present disclosure. As used herein, the term "and/or" includes any and all combinations of one or more of the associated listed items.

It will be understood that when an element is referred to as being "on," "connected to" or "coupled to" another element, it can be directly on, connected to or coupled to the other element or intervening elements may be present. In contrast, when an element is referred to as being "directly on," "directly connected to" or "directly coupled to" another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing particular embodiments and is not intended to be limiting of the invention. As used herein, the singular forms "a," "an" and "the" are intended to include the plural forms as well, unless the context clearly indicates otherwise. It will be further understood that the terms "comprise," "comprises," "comprising," "include," "includes" and/or "including," when used herein, specify the presence of stated features, integers, steps, operations, elements, and/or components, but do not preclude the presence or addition of one or more other features, integers, steps, operations, elements, components, and/or groups thereof.

FIG. 1 is a schematic block diagram illustrating an system 100 for analyzing and medically treating a lumen in a patient 130, according to an embodiment of the present invention. The system 100 includes a catheter 150 with its distal end inserted in the patient 130 and a spectrometer system 120 and user display/interface 110 attached to the proximal end of the catheter 150. In an embodiment, catheter 150 is guided through a patient such as in accordance with a percutaneous transluminal angioplasty procedure and inserted through a patient's femoral artery as illustrated in FIG. 1. In an embodiment, the catheter 150 is the same as or similar to the catheter instruments described herein.

FIG. 2A is an illustrative view of a catheter instrument 200 according to an embodiment of the present invention. FIG. 2B is a cross-sectional view of the catheter instrument 200 of FIG. 2A, taken along section lines I-I' of FIG. 2A. FIG. 2C is a cross-sectional view of the catheter instrument 200 of FIG. 2A, taken along section lines II-II' of FIG. 2A. FIG. 2D is a cross-sectional view of the catheter instrument 200 of FIG. 2A, taken along section lines III-III' of FIG. 2A. In an embodiment, the catheter instrument 200 can be included in the system 100 described above with regard to FIG. 1.

The catheter instrument 200, also referred to as a catheter, includes a catheter body 210, a handle 215, and fiber optic connectors 220 attached to fibers 260 at a proximal end of the catheter 200, which extend through the catheter body 210. The fibers 260 extend to the distal end 250 of catheter 200 and can enable the delivery and/or collection of radiation about distal end 250. The distal end 250 of the catheter 200 has a bend 255 so that the distal end 250 can be more easily manipulated through highly curved lumen areas including, for example, blocked or partially blocked lumens. In an embodiment, the bend 255 is between about a 15 and 45 degree bend. A guidewire 245 passes through an opening 235 into guidewire lumen 230 and exits from the distal end 250 of catheter 200. Radiopaque markers 257 can provide positioning information to a device such as a fluoroscope.

In one embodiment, two delivery fibers 260 and two collection fibers 260 are included. Fiber construction and size can be selected based on parameters relating to the type of analysis being performed, the number and sizes of discrete regions being analyzed, space, strength, and flexibility constraints and/or cost constraints. In various embodiments, the fibers 260 can be constructed of different materials and thicknesses of core, cladding, and jackets. The fibers 260 can also be constructed of graded-index cores in order to increase the numerical aperture and power while retaining small core diameters. Embodiments include graded index fibers of numerical apertures between approximately 0.22 and 0.65. Embodiments include the use of delivery waveguides with core diameters between about 9 and 100 microns and the use of collection waveguides with a fiber core between about 50 and 200 microns. Lucent Technologies Specialty Fiber Group, for example, provides fibers having core diameters between about 62.5 µm to 1500 µm and numerical apertures between about 0.11 to 0.48. Yangtze Optical Fiber and Cable Co., Ltd. of Wuhan, China, see http://yofcfiber.com, the entire contents of which are incorporated herein by reference, provides multi-mode fibers with cores having diameters of 50 microns and maximum outer diameters of 80 microns and single-mode fibers with core diameters of 9 microns and maximum outer diameters of 125 microns.

In an embodiment, fibers 260 include delivery fibers that have a numerical aperture of approximately 0.31, a graded core diameter of approximately 50 micrometers, a cladding layer thickness of approximately 9 to 10 micrometers, and a jacket of approximately 4 to 5 micrometers. In an embodiment, fibers 260 can include collection fibers that are, for example, graded indexed with a core numerical aperture of about 0.22, a core diameter of approximately 100 micrometers, a cladding layer thickness of approximately 10 micrometers, and a jacket thickness of approximately 10 micrometers. Variously sized fibers with relatively high numerical apertures (NAs), e.g. between about 0.22 and 0.65, allow for four-fiber embodiments of a catheter system wherein the maximum outer diameter of catheter body 210 is between about 1.5 and 2 FR or between about 0.5 and 0.67 millimeters (mm). In an embodiment, the catheter can be adapted for larger vessels such as peripheral vessels with catheter diameters of up to about, for example, 4 FR (1.4 mm).

FIG. 3A is an illustrative view of a catheter instrument 300 according to an embodiment of the present invention. FIG. 3B is a cross-sectional view of the catheter instrument of FIG. 3A, taken along section lines I-I' of FIG. 3A. FIG. 3C is a cross-sectional view of the catheter instrument of FIG. 3A, taken along section lines II-II' of FIG. 3A. In an alternative guidewire configuration to that of catheter 200 of FIGS. 2A-2D, the catheter instrument 300 includes a catheter body 310, a handle 315, and fiber optic connectors 320 attached to fibers 360 which extend through catheter body 310. A guidewire 345 is shown passing through an opening 335 at the proximal end of catheter 300 and into guidewire lumen 330, which extends the length of catheter body 310, and then exits from the distal end of catheter 300.

Figure 4A:
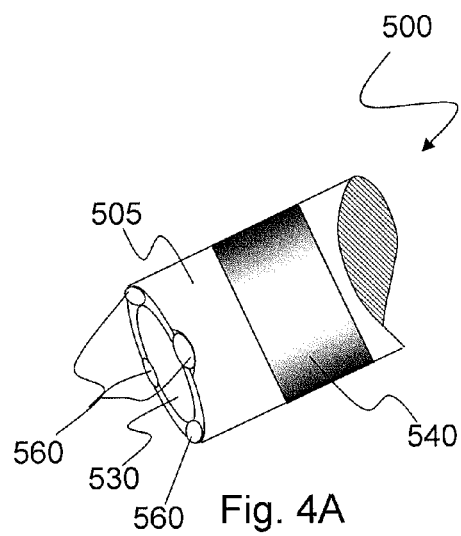
FIG. 4A is an illustrative perspective view of the distal end of a catheter instrument according to an embodiment of the present invention.

FIG. 4A is an illustrative perspective view of the distal end 500 of a catheter instrument according to an embodiment of the present invention. Four fibers ends 560 are generally evenly distributed about the circumference of the catheter body and are generally flush with the distally terminating end 505 of the distal end 500 of the catheter instrument. A guidewire lumen 530 allows for a guidewire (not shown) to exit through distal end 500 and a radiopaque marker 540 enables a detection device (e.g., a fluoroscope) to locate the terminating end 505 of the distal end 500 of the catheter instrument when positioned in a lumen of a patient. In an embodiment, two circumferentially opposing fiber ends 560 are configured for the delivery of light to surrounding fluids and tissue and the remaining fiber ends 560 are configured for the collection of light from surrounding fluids and tissue.

Figure 4B:
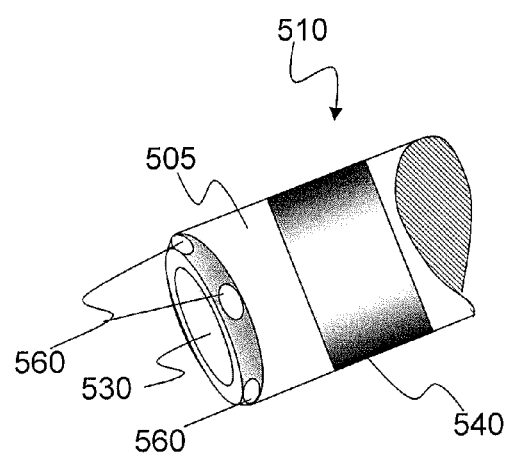
FIG. 4B is an illustrative perspective view of the distal end of a catheter instrument with exposed fiber tip ends according to another embodiment of the present invention.

FIG. 4B is an illustrative perspective view of a distal end 510 of a catheter instrument with fiber tip ends 560 exposed, according to another embodiment. In various embodiments, the fiber tip ends 560 can be manufactured to distribute and/or collect light through the circumferential perimeter of the fiber tip end such as, for example, described in U.S. patent application Ser. No. 12/466,503 filed May 15, 2009 by Jing Tang, entitled "Shaped Fiber Ends and Methods of Making Same," the entire contents of which are herein incorporated by reference.

Figure 4C:
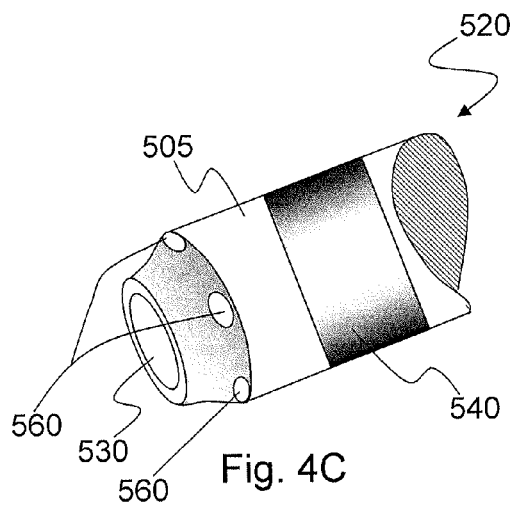
FIG. 4C is an illustrative perspective view of the distal end of a catheter instrument with recessed fiber tips according to another embodiment of the present invention.

FIG. 4C is an illustrative perspective view of the distal end 520 of a catheter instrument with fiber tip ends 560 recessed from the distally terminating end 505 of catheter body 510 according to another embodiment. The tapered distal end 520 can provide a sharpened profile for aiding in the penetration of tissue such as, for example, within a blocked or partially blocked vessel.

Figure 4D:
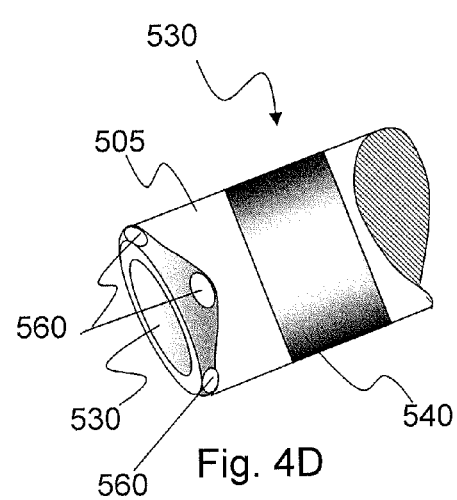
FIG. 4D is an illustrative perspective view of the distal end of a catheter instrument with longitudinally separated fiber tips according to another embodiment of the present invention.

FIG. 4D is an illustrative perspective view of the distal end 530 of a catheter instrument with longitudinally separated fiber tips 560 according to another embodiment of the present invention. Longitudinally separating tips 560 can provide for greater overall separation between tips 560 and can provide deeper and/or more expansive distribution of delivered and collected radiation between tips 560 and targeted tissue and/or fluids.

Figure 5A:
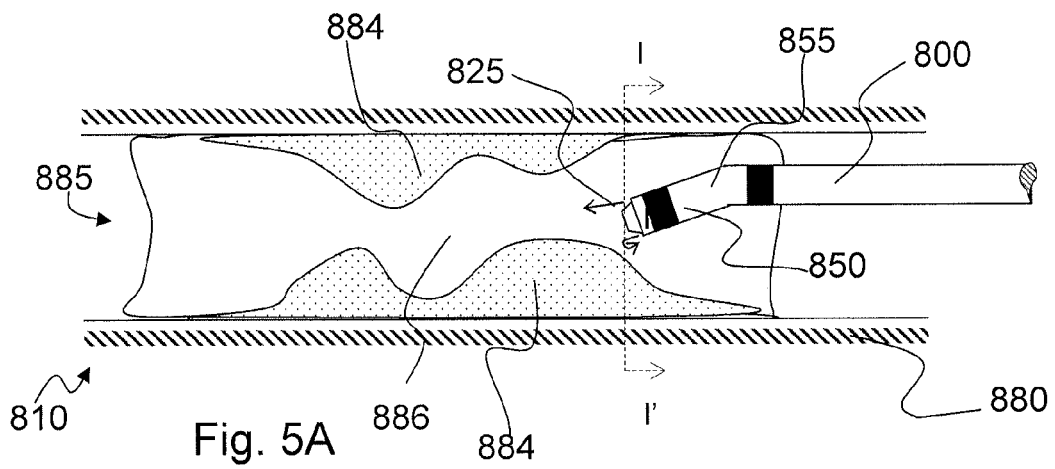
FIG. 5A is an illustrative view of the distal end of an instrument being positioned within a lumen according to an embodiment of the invention.
Figure 5B:
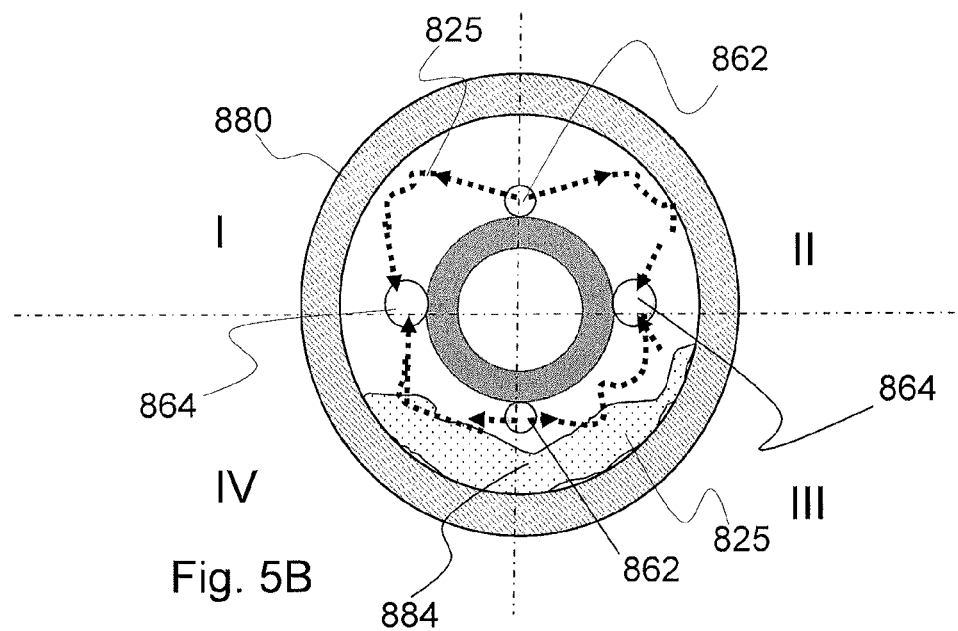
FIG. 5B is a cross-sectional view of the instrument and lumen of FIG. 5A, taken along section lines I-I' of FIG. 5A.
Figure 5C:
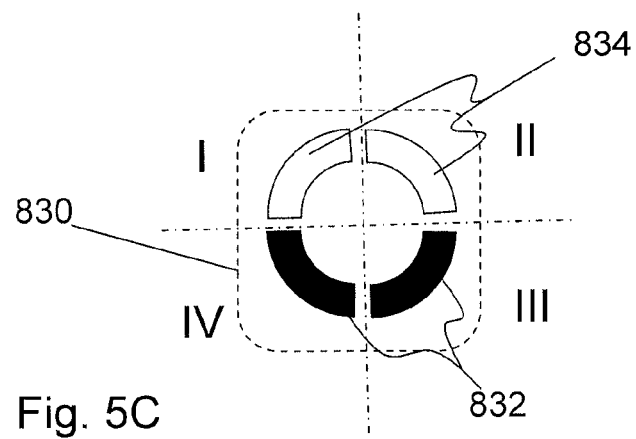
FIG. 5C is an illustrative view of a status display for the instrument of FIG. 5A according to an embodiment of the invention.

FIG. 5A is an illustrative view of the distal end of an instrument 800 being positioned within a lumen 880 according to an embodiment of the invention. FIG. 5B is a cross-sectional view of the instrument 800 and lumen of FIG. 5A, taken along section lines I-I' of FIG. 5A. FIG. 5C is an illustrative view of a status display 830 for the instrument of FIG. 5A according to an embodiment of the invention. Lumen 880 includes an occluded section 885 having a tissue lesion area 884 which can include, for example, high concentrations of vulnerable plaque that, if ruptured by a catheter instrument, such as instrument 800, could lead to serious complications. The occluded area 885 also includes an area 886 with a high concentration of blood components that could include for example, a relatively high concentration of hemoglobin and/or a thrombus or clot that, under appropriate circumstances, would be safely traversable by instrument 800 while area 884 and vessel wall 880 are not penetrated or significantly damaged. FIG. 5B illustrates the lumen divided into four quadrants I, II, III, and IV. Instrument 800 includes delivery fibers 862 and collection fibers 864 which are connected to a source and detector (e.g., the spectrometer 120 of FIG. 1). As instrument 800 is positioned within lumen 880, delivery fibers 862 can deliver radiation about the circumference and forward of probe end 850 such as along exemplary path 825 into the surrounding blood and tissue, after which radiation is transmitted from tissue and blood to a collection fiber 864 and analyzed. The distal end 850 of the catheter 800 has a bend 855 so that the distal end 850 can be more easily manipulated through highly curved lumen areas including, for example, blocked or partially blocked lumens. The surrounding blood and tissue can be analyzed for areas of severe blockage such vulnerable lesions 884 and/or tissue walls and/or areas with high blood content such as areas 886 that could allow safe traversal of the instrument 800.

In an embodiment, spectroscopy is employed with one or more wavelengths with predetermined spectra profiles known to have at least a nominally predictable relationships with the presence of adjacent blood content alone and/or the presence of various chemical components, tissue pathophysiologic or morphological structures, water content, temperature, pH, and color in order to help determine which areas of the lumen are the safest to traverse. In an embodiment, the pathophysiologic or morphologic factors include characterizing the presence, volume, and positioning of plaque, including vulnerable plaque, within the endovascular region. Accidental rupture of a lesion with vulnerable plaque, for example, could lead to serious complications. In an embodiment, regions having higher blood/hemoglobin content are located for potential passage, particularly where complete or partial blood flow occurs.

In another embodiment, the pathophysiologic or morphologic factors further include characteristics of plaque including at least one of collagen content, lipid content, calcium content, inflammation, or the relative positioning of pathophysiologic conditions within the plaque.

In an embodiment of the invention, a source wavelength range can be between about 200 and about 2500 nanometers. In a further embodiment, a source wavelength range can be between about 300 and 1400 nanometers. In a further embodiment, a source wavelength range can be between about 400 and 700 nanometers.

In an embodiment for determining the presence and level of blood/hemoglobin, one or more wavelengths selected from about 407, 532, and between about 800 and 1000 nanometers are spectroscopically analyzed. In an embodiment, diffuse reflectance spectroscopy is used. In an embodiment, ratios and/or other chemometric relationships between two or more of these wavelengths are previously measured at various levels of blood/hemoglobin presence and/or various pathophysiologic or morphologic factors, programmed into a system, and later compared to in-process data collected during an actual procedure. In an embodiment, the one or more wavelengths consist of wavelengths of 532 and 407 nanometers and in another embodiment consist of 532 and 800 nanometers.

In an embodiment for determining the presence and level of blood/hemoglobin, an excitation-inducing wavelength of about 450 nanometers produces a fluorescence excitation emission wavelength in blood/hemoglobin of about 520 nanometers. In an embodiment, a radiation source can be a low-cost LED which is selected to provide a wavelength range between, for example, about 400 and 500 nanometers, concentrating energy at about 450 nanometers. In an embodiment such as, for example, in a single delivery/collection fiber embodiment as described in reference to FIGS. 8G and 10A-10G, collected radiation can be filtered, for example, to pass radiation greater than about 500 nanometers, including 520 nanometer radiation. Upon consideration of the present disclosure, various modified arrangements of filters, sources, and other optical components, optical paths, and wavelength ranges would be apparent to one of ordinary skill in the art.

Status display 830 can provide information about the analysis of the lumen such as, for example, which areas ahead of the instrument within the lumen (e.g., quadrants I, II, III, and/or IV) are traversable with blank indicators 834 or which areas are non-traversable with darkened indicators 832 as shown in FIG. 5C.

FIGS. 6A-6D are illustrative views of the distal end of an instrument 800, also shown in FIGS. 5A-5C, being positioned within a lumen 810 according to an embodiment of the invention. Referring to FIG. 6A, the distal end of instrument 800 is shown approaching occluded area 885 while conducting optical analysis such as, for example, along trace lines 825. If the optical analysis reveals that the probe end 850, if advanced, would significantly damage tissue lesion area 884 or lumen wall 880 such as shown in FIGS. 6A and 6C, the instrument 800 can be manipulated (e.g., rotated), for example, as shown by an arrow, so as to re-position probe end 850 and conduct further optical analysis until the operator can make a determination that advancement of the instrument 800 would be safe. For example, as shown in FIGS. 6A and 6C, status indicator 830, specifically, darkened indicators 832 of status indicator 830, show that the area in front of the lower part of instrument 800 is blocked. The operator can then rotate instrument 800 until display 830 indicates that the area in front of the instrument 800 is clear of blockage and can be safely advanced, as shown by status indicator 830 of FIGS. 6B and 6D.

In other embodiments of previously fiber-optic catheter probes described herein, various additional components can be integrated with the catheter such as, for example, angioplasty catheter components.

FIG. 7A is an illustrative view of an angioplasty balloon catheter instrument 400 according to an embodiment of the present invention. FIG. 7B is a cross-sectional view of the catheter instrument of FIG. 7A, taken along section lines I-I' of FIG. 7A. FIG. 7C is a cross-sectional view of the catheter instrument of FIG. 7A, taken along section lines II-II' of FIG. 7A. FIG. 7D is a cross-sectional view of the catheter instrument of FIG. 7A, taken along section lines III-III' of FIG. 7A.

The catheter instrument 400 includes a catheter body 410, a handle 415, and fiber optic connectors 420 attached to fibers 460 which extend through catheter body 410. A guidewire 445 is shown passing into guidewire lumen 430 and exiting from the distal end 450 of catheter 400. Catheter 400 also includes an angioplasty balloon 440. An interior area 435 of catheter body 410 serves as a flushport for dispensing and removing fluid media to and from balloon 440. In various embodiments, a fiber-optic probe system is integrated with the angioplasty balloon such as described in co-pending U.S. patent application Ser. No. 11/537,258 filed on Sep. 29, 2006, and published as U.S. Patent Application No. US20070078500A1, the entire contents of which are herein incorporated by reference.

Figure 8A:
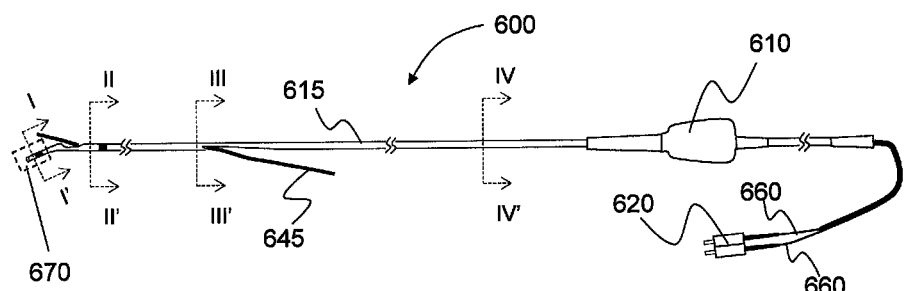
FIG. 8A is an illustrative view of a catheter instrument according to an embodiment of the present invention.
Figures 8B, 8C, 8D, 8E:
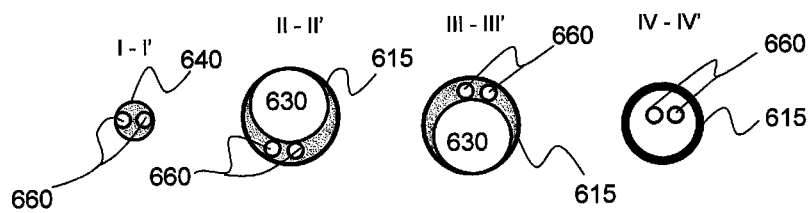
FIG. 8B is a cross-sectional view of the catheter instrument of FIG. 8A, taken along section lines I-I' of FIG. 8A.
FIG. 8C is a cross-sectional view of the catheter instrument of FIG. 8A, taken along section lines II-II' of FIG. 8A.
FIG. 8D is a cross-sectional view of the catheter instrument of FIG. 8A, taken along section lines III-III' of FIG. 8A.
FIG. 8E is a cross-sectional view of the catheter instrument of FIG. 8A, taken along section lines IV-IV' of FIG. 8A.
Figures 8F, 8G:
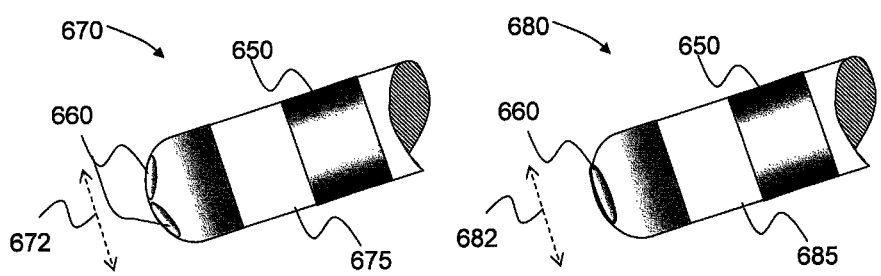
FIG. 8F is an illustrative perspective view of the distal end of the catheter instrument of FIG. 8A.
FIG. 8G is an illustrative perspective view of an alternative distal end of a catheter according to an embodiment of the invention integrated with a single optical fiber.

FIG. 8A is an illustrative view of a catheter instrument 600 according to an embodiment of the present invention. FIG. 8B is a cross-sectional view of the catheter instrument of FIG. 8A, taken along section lines I-I' of FIG. 8A. FIG. 8C is a cross-sectional view of the catheter instrument of FIG. 8A, taken along section lines II-II' of FIG. 8A. FIG. 8D is a cross-sectional view of the catheter instrument of FIG. 8A, taken along section lines III-III' of FIG. 8A. FIG. 8E is a cross-sectional view of the catheter instrument of FIG. 8A, taken along section lines IV-IV' of FIG. 8A. FIG. 8F is an illustrative perspective view of the distal end of the catheter instrument of FIG. 8A. Catheter 600 includes a catheter body 615 through which two fibers 660 extend to the terminating end of tip probe section 670. The fibers used can be of the type used in reference to other embodiments described herein and include one delivery fiber and one collection fiber. Tip probe section 670 is angled so as to allow maneuverability through curved or blocked lumen areas and, in an embodiment, has a maximum outer diameter 672 of about 400 microns. The proximal end of catheter 600 includes a handle and connectors 620 for fibers 660. A guidewire lumen 630 also permits a guidewire 645 to precede or follow catheter 600 to a lumen area. A radiopaque marker 650 permits visualization of the general location of tip probe section 670 within a lumen by a fluoroscope or similar device. In an embodiment, more than two fibers 660 can extend to the terminating end of the tip probe section 670.

FIG. 8G is an illustrative perspective view of an alternative distal end 680 of a catheter according to an embodiment of the invention integrated with a single optical fiber 660. Alternative tip probe section 680 has a single fiber 660 that can act as both a delivery and collection fiber. In an embodiment, the delivered and collected wavelength ranges are non-overlapping such as in accordance with the example cited above for detecting the presence of blood/hemoglobin via fluorescence spectroscopy. Tip probe section 680 and catheter body 615 can thus be manufactured to have even smaller diameters than those of catheter 600 such as, for example, having a catheter body with a maximum outer diameter of less than about 500 microns and the maximum outer diameter 682 of the tip section 680 being less than 400 microns.

Figure 9A:
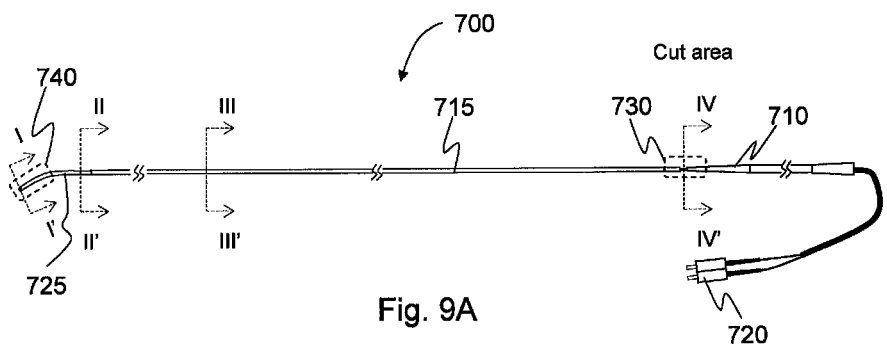
FIG. 9A is an illustrative view of a guidewire instrument according to an embodiment of the present invention.
Figures 9B, 9C, 9D, 9E:
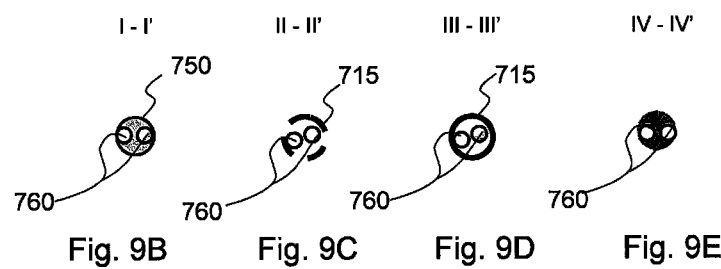
FIG. 9B is a cross-sectional view of the guidewire instrument of FIG. 9A, taken along section lines I-I' of FIG. 9A.
FIG. 9C is a cross-sectional view of the guidewire instrument of FIG. 9A, taken along section lines II-II' of FIG. 9A.
FIG. 9D is a cross-sectional view of the guidewire instrument of FIG. 9A, taken along section lines III-III' of FIG. 9A.
FIG. 9E is a cross-sectional view of the guidewire instrument of FIG. 9A, taken along section lines IV-IV' of FIG. 9A.
Figures 9F, 9G:
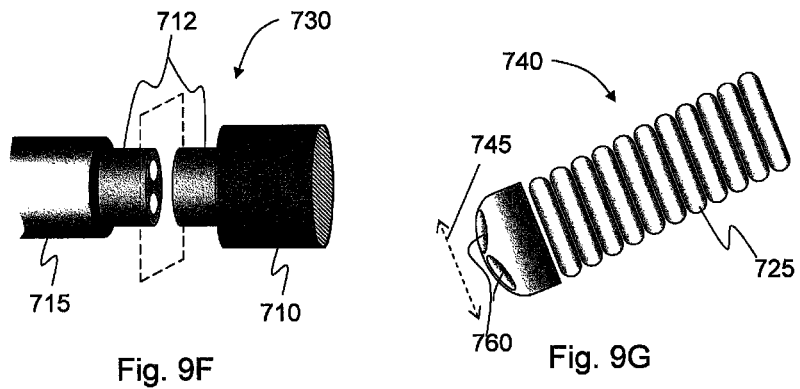
FIG. 9F is an illustrative perspective view of a detachable section of the guidewire instrument of FIG. 9A.
FIG. 9G is an illustrative perspective view of the distal end of the guidewire instrument of FIG. 9A.

FIG. 9A is an illustrative view of a guidewire instrument 700 according to an embodiment of the present invention. FIG. 9B is a cross-sectional view of the guidewire instrument of FIG. 9A, taken along section lines I-I' of FIG. 9A. FIG. 9C is a cross-sectional view of the guidewire instrument of FIG. 9A, taken along section lines II-II' of FIG. 9A. FIG. 9D is a cross-sectional view of the guidewire instrument of FIG. 9A, taken along section lines III-III' of FIG. 9A. FIG. 9E is a cross-sectional view of the guidewire instrument of FIG. 9A, taken along section lines IV-IV' of FIG. 9A. FIG. 9F is an illustrative perspective view of a detachable section of the guidewire instrument of FIG. 9A. FIG. 9G is an illustrative perspective view of the distal end of the guidewire instrument of FIG. 9A.

Guidewire instrument 700 includes a guidewire body 715 through which fibers 760 extend to the terminating end of tip probe section 740. In an embodiment, one of the fibers 760 is designated as a delivery fiber and one of fibers 760 is designated as a collection fiber. The fibers 760 used can be of the type used in reference to other embodiments described herein. In an embodiment, the maximum outer diameter 745 of guidewire body 715 is about 400 microns or less. The proximal end 710 of guidewire instrument 700 includes fiber connectors 720 which are connected to fibers 760. Guidewire body 715 of guidewire instrument 700 includes a section 712 allowing for disconnecting proximal end 710 from the remaining parts of the guidewire. After using the optical probe component of guidewire instrument 700 to optimally position the guidewire instrument 700 within a lumen (not shown), the proximal end 710 could be detached so that, for example, the guidewire instrument 700 can be used to position a catheter (e.g., an angioplasty catheter) into position. In an embodiment, proximal end 710 can also be reattached so as to re-position guidewire instrument 700 with the use of the optical probe components. The distal end of guidewire instrument 700 includes a highly flexible segment 725. Segment 725 can comprise, for example, a body of highly thin wire wrapped in a helical formation. In an embodiment, the distal end of guidewire instrument 700 includes a segment 740 which is pre-shaped to bend off-axis so as to improve maneuverability in highly curved or blocked lumen areas.

Figure 10A:
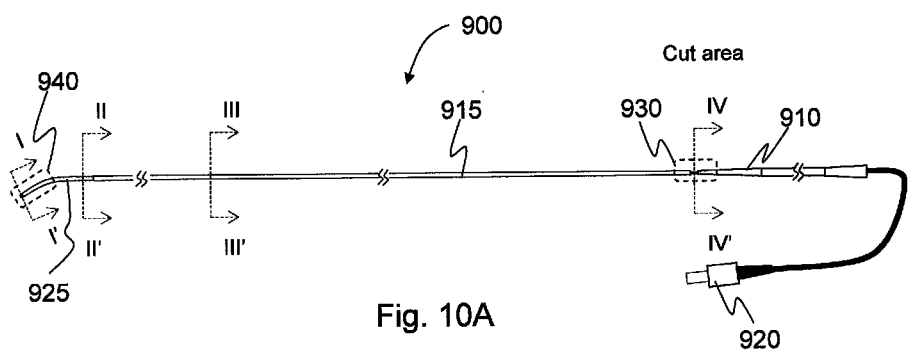
FIG. 10A is an illustrative view of a guidewire instrument according to an embodiment of the present invention integrated with a single optical fiber.
Figures 10B, 10C, 10D, 10E:
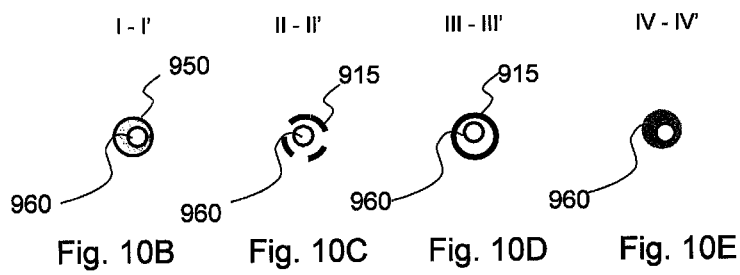
FIG. 10B is a cross-sectional view of the guidewire instrument of FIG. 10A, taken along section lines I-I' of FIG. 9A.
FIG. 10C is a cross-sectional view of the guidewire instrument of FIG. 10A, taken along section lines II-II' of FIG. 10A.
FIG. 10D is a cross-sectional view of the guidewire instrument of FIG. 10A, taken along section lines III-III' of FIG. 10A.
FIG. 10E is a cross-sectional view of the guidewire instrument of FIG. 10A, taken along section lines IV-IV' of FIG. 10A.
Figures 10F, 10G:
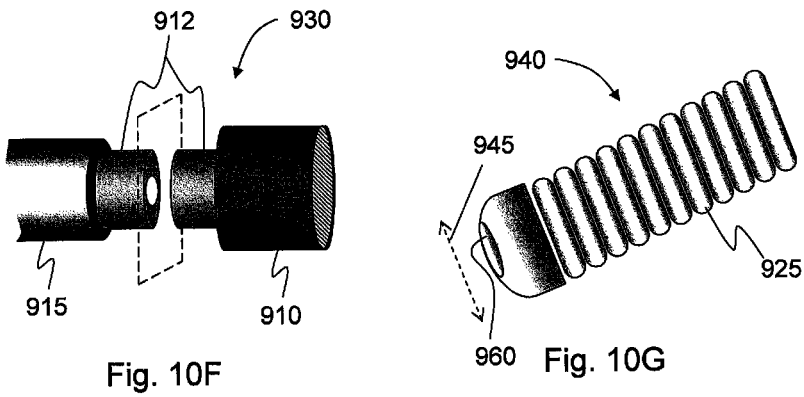
FIG. 10F is an illustrative perspective view of a detachable section of the guidewire instrument of FIG. 10A.
FIG. 10G is an illustrative perspective view of the distal end of the guidewire instrument of FIG. 10A.

FIG. 10A is an illustrative view of a guidewire instrument 900 according to an embodiment of the present invention integrated with a single optical fiber 960. FIG. 10B is a cross-sectional view of the guidewire instrument of FIG. 10A, taken along section lines I-I' of FIG. 9A. FIG. 10C is a cross-sectional view of the guidewire instrument of FIG. 10A, taken along section lines II-II' of FIG. 10A. FIG. 10D is a cross-sectional view of the guidewire instrument of FIG. 10A, taken along section lines III-III' of FIG. 10A. FIG. 10E is a cross-sectional view of the guidewire instrument of FIG. 10A, taken along section lines IV-IV' of FIG. 10A. FIG. 10F is an illustrative perspective view of a detachable section of the guidewire instrument of FIG. 10A. FIG. 10G is an illustrative perspective view of the distal end of the guidewire instrument of FIG. 10A.

Guidewire instrument 900 includes a guidewire body 915 through which a fiber 860 extends to the terminating end of tip probe section 940. The fiber 960 used can be of the type used in reference to other embodiments described herein that use a single fiber acting as both a delivery and collection fiber. In an embodiment, the maximum outer diameter 845 of guidewire body 915 is about 400 microns or less and, in an embodiment, about 300 microns or less. The proximal end 810 of guidewire instrument 900 includes a fiber connector 920 which are connected to fiber 960. Guidewire body 915 of guidewire instrument 900 includes a segment 930 with disconnecting sections 912 for separating proximal end 910 from the remaining parts of the guidewire instrument 900. After using the optical probe component of guidewire instrument 900 to optimally position the guidewire instrument 900 within a lumen (not shown), the proximal end 910 could be detached so that, for example, the guidewire instrument 900 can be used to position a catheter (e.g., an angioplasty catheter) into position. In an embodiment, proximal end 910 can also be reattached so as to re-position guidewire instrument 900 with the use of the optical probe components. The distal end of guidewire instrument 900 includes a highly flexible segment 925. Segment 925 can comprise, for example, a body of highly thin wire wrapped in a helical formation. In an embodiment, the distal end of guidewire instrument 900 includes a segment 940 which is pre-shaped to bend off-axis so as to improve maneuverability in highly curved or blocked lumen areas.

While embodiments of the invention have been particularly shown and described above, it will be understood by those skilled in the art that various changes in form and detail may be made herein without departing from the spirit and scope of the invention as defined by the appended claims.

I claim:

1. A catheter instrument, comprising:
   a flexible conduit that is suitable for insertion into an occluded body lumen, the conduit elongated along a longitudinal axis and having a proximal end and a distal end, the conduit constructed and arranged for rotating about a longitudinal axis extending along the body lumen during at least one of a probe or a treatment of the occluded body lumen; and
   at least one delivery waveguide and at least one collection waveguide integrated with the flexible conduit and constructed and arranged to deliver and collect radiation about the distal end of said flexible conduit, wherein the at least one delivery waveguide and at least one collection waveguide are configured to scan and collect radiation over a cross-section of the body lumen path longitudinally beyond the distal end of said flexible conduit.

2. The catheter instrument of claim 1, wherein the radiation is provided at a wavelength in a range of about 250 to 2500 nanometers.

3. The catheter instrument of claim 2, wherein the catheter instrument outputs data corresponding to the scanned and collected radiation to a spectrometer constructed and arranged to perform spectroscopy at the wavelength of the radiation, said spectrometer configured to perform spectroscopy of at least one of the methods comprising fluorescence, light scatter, speckle correlometry, Raman, and diffuse reflectance spectroscopy.

4. The catheter instrument of claim 1 wherein the collected radiation includes data indicating the presence of blood components longitudinally beyond the distal end of said flexible conduit.

5. The catheter instrument of claim 4 wherein said blood components comprise hemoglobin.

6. The catheter instrument of claim 1, wherein said at least one delivery waveguide is configured to output radiation including a wavelength of 450 nanometers and wherein the at least one collection waveguide is configured and arranged to output a fluorescence radiation including a wavelength of about 520 nanometers.

7. The catheter instrument of claim 1, wherein said flexible conduit further comprises an angioplasty balloon.

8. The catheter instrument of claim 1, wherein said flexible conduit has a maximum outer diameter of between about 0.5 and about 0.67 millimeters.

9. The catheter instrument of claim 1, wherein said flexible conduit has a maximum outer diameter of less than about 0.5 millimeters.

10. The catheter instrument of claim 1, wherein said flexible conduit is a guidewire.

11. The catheter instrument of claim 10, wherein said guidewire comprises one or more fiber connectors detachable from the proximate end of said guidewire so as to allow said guidewire to completely pass through a catheter.

12. The catheter instrument of claim 1, wherein said flexible conduit has a maximum outer diameter of about 0.3 millimeters or less.

13. A catheter instrument, comprising:
   a flexible conduit that is suitable for insertion into an occluded body lumen, the conduit elongated along a longitudinal axis and having a proximal end and a distal end, the conduit constructed and arranged for rotating about a longitudinal axis extending along the body lumen during at least one of a probe or a treatment of the occluded body lumen; and
   at least one delivery waveguide and at least one collection waveguide integrated with the flexible conduit and constructed and arranged to deliver and collect radiation about the distal end of said flexible conduit, wherein the at least one delivery waveguide and at least one collection waveguide are configured to scan and collect radiation longitudinally beyond the distal end of said flexible conduit, wherein said flexible conduit includes a distal end with a portion pre-bent at an angle so as to allow increased maneuverability through the occluded body lumen.

14. The catheter instrument of claim 13, wherein the portion pre-bent at an angle is bent at an angle between 15 and 45 degrees.

15. The catheter instrument of claim 1, wherein the at least one delivery waveguide and at least one collection waveguide comprise fiber optic tips manufactured to emit or collect radiation circumferentially around approximately 90 degrees or more of the end of the fiber optic tips.

16. The catheter instrument of claim 1, wherein a transmission output of at least one delivery waveguide is longitudinally separated from a transmission input of at least one collection waveguide.

17. The catheter instrument of claim 1, wherein said at least one delivery waveguide and at least one collection waveguide consist of a single waveguide.

18. The catheter instrument of claim 1, wherein said flexible conduit further comprises an angioplasty balloon.

19. The catheter instrument of claim 1, wherein the flexible conduit is constructed and arranged to execute at least one of a treatment procedure and an analysis procedure.

20. The catheter instrument of claim 19, wherein the at least one of a treatment procedure and an analysis procedure includes at least one of an intravascular ultrasound (IVUS) procedure, an optical coherence tomography (OCT) procedure, and an angioplasty procedure.

21. The catheter instrument of 19, wherein the at least one of a treatment procedure and an analysis procedure includes an occluded-lumen traversal procedure.

22. The catheter instrument of 21, wherein the occluded-lumen traversal procedure includes an atherectomy.

23. A method for directing a flexible conduit through obstacles within an occluded body lumen, the method comprising:
    inserting the flexible conduit into the occluded body lumen, said flexible conduit integrated with at least one delivery waveguide arranged to deliver radiation about a distal end of said conduit and at least one collection waveguide arranged to collect radiation about the distal end of said conduit;
    rotating the conduit about a longitudinal axis in proximity to a region of the occluded body lumen;
    scanning and collecting radiation over a cross-section of the body lumen path longitudinally beyond the distal end of said flexible conduit; and
    determining whether to advance the conduit in the occluded body lumen by further rotating the conduit in response to data corresponding to the scanned and collected radiation by analyzing data corresponding to the scanned and collected radiation.

24. The method of claim 23, further comprising executing a spectroscopic analysis of the occluded body lumen using radiation at a wavelength in a range of about 250 to 2500 nanometers by radiating areas of the occluded body lumen with the radiation that is supplied at the transmission output of the at least one delivery waveguide, the supplied radiation distributed about the distal end of said flexible conduit, and wherein radiation is returned to the transmission input of the at least one collection waveguide, said spectroscopic analysis comprising at least one of fluorescence, light scatter, speckle correlometry, Raman, and diffuse reflectance spectroscopy.

25. The method of claim 23, wherein said distal end of said flexible conduit includes a portion pre-bent that is at an angle so as to allow increased maneuverability through said occluded lumen, and wherein further rotating the flexible conduit comprises rotating said pre-bent portion toward an area identified as traversable.

26. The method of claim 23, further comprising scanning and collecting radiation about a circumference of the distal end of said flexible conduit.

27. The method of claim 23, wherein the flexible conduit is constructed and arranged to execute at least one of a treatment procedure and an analysis procedure.

28. The method of claim 27, wherein the at least one of a treatment procedure and an analysis procedure includes at least one of an intravascular ultrasound (IVUS) procedure, an optical coherence tomography (OCT) procedure, and an angioplasty procedure.

29. The method of claim 27, wherein the at least one of a treatment procedure and an analysis procedure includes an occluded-lumen traversal procedure.

30. The method of claim 29, wherein the occluded-lumen traversal procedure includes anatherectomy.

* * * * *